United States Patent [19]

Chaudhuri et al.

[11] Patent Number: 4,713,463
[45] Date of Patent: Dec. 15, 1987

[54] SYNTHESIS OF N-EPOXYPROPYL LACTAMS

[75] Inventors: Ratan K. Chaudhuri, Butler; Robert B. Login, Oakland; David J. Tracy, Lincoln Park, all of N.J.

[73] Assignee: GAF Corporation, Wayne, N.J.

[21] Appl. No.: 922,922

[22] Filed: Oct. 24, 1986

[51] Int. Cl.$^4$ .................. C07D 207/12; C07D 223/10; C07D 211/40
[52] U.S. Cl. .................................. 548/517; 540/524; 546/207
[58] Field of Search .......... 546/207; 549/553; 548/517; 540/524

[56] References Cited

U.S. PATENT DOCUMENTS 2,520,093 8/1950 Gross .............................. 546/207 X
3,144,417 8/1964 Bailey, Jr. et al. ............. 546/207 X

OTHER PUBLICATIONS

Dehmlow et al.; "Phase Transfer Catalysis" (1980), pp. 93–98, Weinheim; Deerfield Beach, Fla., Basel.
C.A. 68: 104970m; Sidel' Kovskaya et al. (1968).
C.A. 85: 32745t; Sidel' Kovskaya et al. (1976).
C.A. 77: 152639t; Mukhitdinova et al. (1972).

*Primary Examiner*—Joseph Paul Brust
*Attorney, Agent, or Firm*—Marilyn J. Maue; Joshua J. Ward

[57] ABSTRACT

The single stage process of reacting a lactam with an epihalohydrin in the presence of alkali metal hydroxide and between about $10^{-1}$ and about $10^{-4}$ molar concentration based on lactam of a phase transfer catalyst selected from the group of tetraalkyl ammonium hydrogen sulfate and tetraalkyl ammonium halide.

8 Claims, No Drawings

SYNTHESIS OF N-EPOXYPROPYL LACTAMS

BACKGROUND OF THE INVENTION

N-epoxyalkyl lactams, particularly N-epoxypropyl-2-pyrrolidone, are valuable surfactant intermediates widely used in cosmetic and pharmaceutical arts. The pyrrolidone compound has been previously synthesized by reacting potassium pyrrolidone and epichlorohydrin in diethyl ether (E. P. Sidelkovkaya et al., Chim. Geterosiki Soevin, #2, page 212, 1968). However this method requires the preparation of potassium pyrrolidone from potassium hydroxide which involves azeotropic removal of water and extensive ring opening of the pyrrolidone component which is highly undesirable. Additionally, the reaction of potassium pyrrolidone with epichlorohydrin requires the use of a solvent which greatly increases the cost of producing product. An alternative method, involving reaction with potassium t-butoxide is also prohibitively expensive and the low yields resulting from the above syntheses makes them unattractive for commerical use.

Accordingly, it is an object of the present invention to overcome the above deficiencies and to provide a commercially feasible process for the preparation of a N-epoxypropyl lactam in high yield.

Another object of the invention is to provide a one step process which is suitable for large scale production of N-epoxypropyl pyrrolidone.

These and other objects will become apparent from the following description and disclosure.

THE INVENTION

According to this invention a lactam having from 4 to 6 carbon atoms, such as pyrrolidone, piperidone or caprolactam is reacted with an epihalohydrin, preferably epichlorohydrin, in the presence of an alkali metal hydroxide, preferably sodium or potassium hydroxide, and between about $10^{-1}$ and about $10^{-4}$ molar concentration based on lactam of a phase transfer catalyst having the formulae:

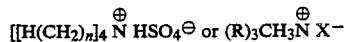

wherein n is an integer having a value between 3 and 10; R is alkyl having from 4 to 12 carbon atoms and $X^-$ is $Cl^-$ or $Br^-$.

Generally, the reaction is effected at a temperature of between about 30° and about 75° C. over a period of from about 5 to about 30 hours; preferably at a temperature between about 32° and about 50° C. for a period of 1 to 18 hours under atmospheric pressure.

The above catalysts, of which the tetrabutyl- and tetraoctyl-ammonium hydrogen sulfates are preferred, can be employed in an amount between about $10^{-1}$ and about $10^{-4}$ molar concentration based on lactam. However, a catalytic amount of from about $10^{-2}$ molar and about $10^{-3}$ molar is usually sufficient to promote and complete the reaction within a resonable period of time.

The epihalohydrin employed in the reaction is preferably epichlorohydrin although epibromohydrin may also be employed, and this reactant is employed in a mole ratio of the epihalohydrin to lactam between about 5:1 and about 1:1, although a slight excess of the former is usually desired. Mole ratios of between about 4-2:1 have been found to be highly effective in producing product in high yield within a period of from about 1 to about 12 hours.

While the order of addition for the reactants is not critical in the present process, it is desirable that they be contacted in incremental amounts over a substantial period; usually dropwise addition of the lactam over a period of several hours is most effective and is convenient for maintaining the exothermic reaction within the above temperature range.

It is recommended that the metal hydroxide employed in the reaction be highly concentrated. While aqueous solutions having a hydroxide concentration as low as 60% can be employed without detriment to the reaction, removal of water at completion of the reaction significantly increases the cost of the process and should be avoided. Accordingly, in the process of this invention, an alkali metal hydroxide concentration of between about 80 and 100% is recommended. The metal hydroxide can be employed as pellets, flakes or as a concentration aqueous solution and is generally used in molar amount of from about 1:1.5 to about 1.5:1 with respect to the epihalohydrin; about equimolar amounts being preferred.

Upon completion of the reaction, the resulting mixture is filtered and washed free of metal sulfate with methylene chloride, ethyl acetate, toluene, benzene, or chloroform, etc. The resulting mixture is filtered and the filtrate distilled to remove excess epihalohydrin and other low boiling impurities. The desired product is further subjected to vacuum distillation to recover product in yields greater than 70%.

Having thus described the present invention, reference is now had to the following Examples which illustrated preferred embodiments but which are not to be construed as limiting to the scope of the invention as more broadly as set forth above and in the appended claims.

EXAMPLE 1

To a 2 liter, 4-neck flask equipped with stirrer, reflux condenser, thermometer, and dropping funnel containing epichlorohydrin (329 ml., 4 moles) was added with stirring sodium hydroxide (pellets, 160 g, 4 moles) and water (16 ml.)

Tetrabutyl ammonium hydrogen sulfate (4.4 g, 0.013 mole) was then introduced during agitation.

This reaction mixture was stirred at room temperature for 15 minutes and the reaction exothermed to about 35° C. To the above reaction mixture 2-pyrrolidone (76 ml., 1 mole) was then added dropwise over a period of two hours. The resulting exothermic reaction was maintained between 35°–45° C. using ice water bath. After completion of the 2-pyrrolidone addition, the reaction mixture was stirred for an additional 5 hours and filtered and filtrate collected. The precipitated salts were washed with methylene chloride ($4 \times 100$ ml.). The filtrate and the methylene chloride washings were combined, dried over anhydrous sodium sulfate, and again filtered to remove sodium sulfate. The filtrate was stripped in the rotary evaporator to remove methylene chloride and the residue (317.1 g) was placed in a distillation flask where, at a temperature of 30°–75° C. and about 0.25 mm Hg, the excess epichlorohydrin and the other low-boiling impurities are removed. The desired epoxide product was obtained at 90°–95° C. (0.2 mm Hg) and in 75% yield. The structure of this compound

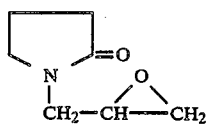

was confirmed by $^{13}$C and $^1$H NMR data.

EXAMPLE 2

The reaction of Example 1 was repeated except that only 2 moles of 2-pyrrolidone was employed. Using the same reaction conditions and work-up procedure, the same epoxide product was recovered in 72% yield.

EXAMPLE 3

The reaction of Example 1 was repeated except that tricaprylmethylammonium chloride was used as phase transfer catalyst and was reacted for 1 hour. The product 2,3-epoxypropylpyrrolidone was isolated in 73% yield by distillation.

It is to be understood that other lactam species, such as piperidone or caprolactam can be substituted in the above examples to provide the corresponding epoxy propyl products in high yield and purity. Also, epibromohydrin can be substituted for the chlorohydrin to provide equivalent product yield and purity.

These and other embodiments of the invention will become apparent and are included in the scope of this invention.

What is claimed is:

1. The liquid phase process which comprises epoxylating a lactam having from 4 to 6 carbon atoms with an epihalohydrin selected from the group of epichlorohydrin and epibromohydrin in the presence of an aqueous alkali metal hydroxide solution employed in a concentration at least as high as 60% or in the presence of 100% alkali metal hydroxide and a quaternized catalyst selected from the group having the formulae:

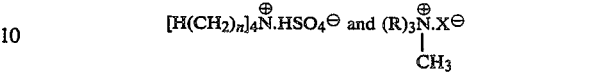

wherein n is an integer having a value of from 3 to 10; R is alkyl having from 4 to 12 carbon atoms and $X^-$ is $Cl^-$ or $Br^-$, to produce the corresponding N-epoxypropyl lactam.

2. The process of claim 1 wherein the lactam is 2-pyrrolidone.

3. The process of claim 1 wherein the epihalohydrin is epichlorohydrin.

4. The process of claim 1 wherein the catalyst is tetrabutyl ammonium hydrogen sulfate.

5. The process of claim 1 wherein the alkali metal hydroxide is sodium or potassium hydroxide.

6. The process of claim 5 wherein the metal hydroxide is used in the form of pellets.

7. The process of claim 1 which is effected at a temperature of between about 30° and about 75° C.

8. The process of claim 7 which is effected at a temperature of between about 32° and about 50° C. under atmospheric pressure.

* * * * *